United States Patent [19]
Burnham et al.

[11] Patent Number: 6,066,468
[45] Date of Patent: May 23, 2000

[54] CHROMOSOMAL DNA FRAGMENTS ENCODING ENZYMES FOR ENCODING β-LACTAM BIOSYNTHETIC ENZYMES, AND VECTORS AND TRANSFORMANTS FOR THEIR EXPRESSION

[75] Inventors: Martin Karl Russel Burnham, Betchworth; Ian David Normansell, Worthing; John Edward Hodgson, Betchworth, all of United Kingdom

[73] Assignee: Beecham Group plc, Brentford, United Kingdom

[21] Appl. No.: 08/477,858

[22] Filed: Jun. 7, 1995

Related U.S. Application Data

[63] Continuation of application No. 08/292,060, Aug. 17, 1994, abandoned, which is a continuation of application No. 08/147,041, Nov. 3, 1993, abandoned, which is a continuation of application No. 08/004,785, Jan. 14, 1993, abandoned, which is a continuation of application No. 07/632,630, Dec. 26, 1990, abandoned, which is a continuation of application No. 07/008,637, Jan. 29, 1987, abandoned.

[30] Foreign Application Priority Data

| Jan. 31, 1986 | [GB] | United Kingdom | 8602441 |
| Feb. 22, 1986 | [GB] | United Kingdom | 8604439 |
| May 17, 1986 | [GB] | United Kingdom | 8612057 |

[51] Int. Cl.$^7$ .............. C12N 9/02; C12N 9/90; C12N 15/53; C12N 15/61
[52] U.S. Cl. .......... 435/69.1; 435/233; 435/189; 435/252.3; 435/252.35; 435/320.1; 536/23.2
[58] Field of Search .................. 435/183, 189, 435/194, 69.1, 252.3, 252.33, 252.35, 320.1, 235; 536/23.2

[56] References Cited

U.S. PATENT DOCUMENTS

| 3,862,008 | 1/1975 | Hamill et al. | 435/47 R |
| 4,510,246 | 4/1985 | Wolfe et al. | 435/183 |
| 4,536,476 | 8/1985 | Wolfe et al. | 435/183 |
| 4,693,977 | 9/1987 | Wolfe et al. | 435/180 |
| 4,762,786 | 8/1988 | Chapman et al. | 435/172.3 |

(List continued on next page.)

OTHER PUBLICATIONS

Kovacevic, S., et al., Journal of Bacteriology, vol. 172, "The B–lactam biosynthesis genes for isopenicillin N epimerase and deacetoxycephalosporin C synthetase are expressed from a single transcript in *Streptomyces clavuligerus*", pp. 3952–3958, 1990.

Jensen, S. E., et al., Canadian Journal of Microbiology, vol. 29, "Rapid purification and characterization of isopenicillin N epimerase activity from *Streptomyces clavuligerus*", pp. 1526–1531, 1983.

Chater, K.F., et al., Current Topics in Microbiology and Immunology, vol. 96, "Gene Cloning in Streptomyces", pp. 69–95, 1982.

Katz, E., et al., Journal of General Microbiology, vol. 129, "Cloning and Expression of the Tyrosinase Gene from *Streptomyces antibioticus* in *Streptomyces lividans*", pp. 2703–2714, 1983.

Feitelson, J. S., et al., Molecular and General Genetics, vol. 190, "Cloning of a Streptomyces Gene for an O–Methyltransferase Involved in Antibiotic Biosynthesis", pp. 394–398, 1983.

(List continued on next page.)

*Primary Examiner*—Ponnathapu Achutamurthy
*Assistant Examiner*—William W. Moore
*Attorney, Agent, or Firm*—Zoltan Kerekes; Stephen Venetianer; Charles M. Kinzig

[57] ABSTRACT

DNA sequences obtained from *S. clavuligerus* ATCC 27064, recombinant vectors incorporating such sequences and hosts transformed with such vectors are disclosed. The DNA comprises one or more genes coding for one or more enzymes involved in the biosynthesis of penicillin and cephalosporin β-lactams and such enzymes are expressed by hosts into which the recombinant vectors are transformed. The DNA and the enzymes encoded thereby have utility in the preparation of penicillins and cephalosporins, both known and novel, possessing pharmacological, especially antimicrobial, activity.

29 Claims, 3 Drawing Sheets

U.S. PATENT DOCUMENTS

| | | | |
|---|---|---|---|
| 4,847,200 | 7/1989 | Wolfe et al. | 435/43 |
| 4,885,251 | 12/1989 | Ingolia et al. | 435/183 |
| 4,892,819 | 1/1990 | Carr et al. | 435/69.1 |
| 4,935,340 | 6/1990 | Baltz et al. | 435/6 |
| 5,070,020 | 12/1991 | Ingolia et al. | 435/183 |
| 5,082,772 | 1/1992 | Dotzlaf et al. | 435/29 |
| 5,318,896 | 6/1994 | Conder et al. | 435/47 |
| 5,559,005 | 9/1996 | Condor et al. | 435/47 |
| 5,629,171 | 5/1997 | Condor et al. | 435/47 |
| 5,714,363 | 2/1998 | Yeh et al. | 435/189 |
| 5,726,032 | 3/1998 | Bovenberg et al. | 435/51 |
| 5,731,165 | 3/1998 | Bovenberg et al. | 435/47 |
| 5,795,733 | 8/1998 | Bovenberg et al. | 435/51 |

OTHER PUBLICATIONS

Martin, J. F., et al., Bio/Technology, vol. 4, "Cloning and Expression of Antiobiotic Production Genes", pp. 64–72, 1984.

Malpartida, F., et al., Nature, vol. 309, "Molecular cloning of the whole biosynthetic pathway of a Streptomyces antibiotic and its expression in a heterologous host", pp. 462–464, 1984.

Bailey, C. R., et al., Bio/Technology, vol. 4, "Cloning a *Streptomyces clavuligerus* Genetic Locus Involved in Clavulkanic Acid Biosynthesis", pp. 808–811, 1984.

Lathe, Richard, Journal of Molecular Biology, vol. 183, "Synthetic Oligonucleotide Probes Deduced from Amino Acid Sequence Data, Theoretical and Practical Considerations", pp. 1–12, 1985.

Samson, S. M., et al., Nature, vol. 318, "Isolation, sequence determination and expression in *Escherichia coli* of the isopenicillin N synthetase gene from *Cephalosporium acremonium*", pp. 191–194, 1984.

Carr, L. G., et al., Gene, vol. 48, "Cloning and expression of the isopenicillin N synthetase gene from *Penicillium chrysogenum*", pp. 257–266, 1986.

Chater, K. F. and Hopwood, D. A., "Antibiotic Biosynthesis in Streptomyces", in Genetics of Bacterial Diversity, Hopwood et al., Eds., Academic Press, pp. 129–150, 1989.

Hewick, R. M., et al., The Journal of Biological Chemistry, vol. 256, No. 15, "A Gas–Liquid Solid Phase Peptide and Protein Sequenator", pp. 7990–7997, 1981.

Matsuda, G., et al., FEBS Letters, vol. 126, "The Primary Structure of L–1 Light Chain of Chicken Fast Skeletal Muscle Myosin and Its Genetic Implication", pp. 111–113, 1981.

Jensen et al., "Analysis of Penicillin N Ring Expansion . . . ", *Antimicrobial Agents and Chemotherapy*, Sep. 1983, p. 307–312.

Jensen et al., "Deacetoxycephalosporin C Synthetase . . . ", *J. Antibiotics*, vol. XXXVIII, No. 2, Feb. 1985, p. 263–265.

D.A. Hopwood, "Cloning Streptomyces genes for antibiotic production," *Trends in Biotech.*, vol. 1, No. 2 (1983).

CHROMOSOMAL DNA FRAGMENTS ENCODING ENZYMES FOR ENCODING β-LACTAM BIOSYNTHETIC ENZYMES, AND VECTORS AND TRANSFORMANTS FOR THEIR EXPRESSION

This application is a continuation of application Ser. No. 292,060, filed Aug. 17, 1994, now abandoned, which is a continuation of application Ser. No. 147,041, filed Nov. 3, 1993, now abandoned, which is a continuation of application Ser. No. 4,785, filed Jan. 14, 1993, now abandoned, which is a continuation of application Ser. No. 632,630, filed Dec. 26, 1990, now abandoned, which is a continuation of application Ser. No. 8,637, filed Jan. 29, 1987, now abandoned.

The present invention relates to recombinant DNA molecules, and in particular to recombinant vectors for use in the transformation of a microbial host which contain inserted DNA fragments carrying one or more genes coding for one or more enzymes involved in the biosynthesis of β-lactam antibiotics, especially penicillins and cephalosporins.

Progress in understanding the biosynthesis of β-lactam antibiotics produced by micro-organisms such as *Streptomyces clavuligerus* has been slow. Nevertheless it has been established that the biosynthetic pathways of certain penicillins and cephalosporins (including cephamycins) are closely related.

Isopenicillin N is an intermediate in the biosynthesis of both groups of compounds and is formed by the action of a 'cyclase' enzyme on the tripeptide δ(L-α-aminoadipyl)-L-cysteinyl-D-valine (sometimes referred to as LLD-ACV or, more simply, ACV as used hereinbelow). The intermediate isopenicillin N may be converted either into penicillin G or, by the action of an 'epimerase' enzyme, into penicillin N and it is from the latter that various cephalosporins and cephamycins may be derived by a multi-step pathway following an initial ring-expansion with an 'expandase' enzyme. A recent summary of the state of the art is given by J. F. Martin and P. Liras in *Trends in Biotechnology*, 1985, 3, 39–44. Thus, in the biosynthesis of Cephamycin C, penicillin N is converted into deacetoxycephalosporin C which is then converted by a dioxygenase enzyme into desacetylcephalosporin C.

The latter is O-carbamoylated to give O-carbamoyldesacetylcephalosporin C, which is then converted into Cephamycin C. It is probable, in the light of work by J. D. Hood et al. (*J. Chem. Soc., Chem. Commun*, 1983, pages 1187–1168 and references therein) that the 7α-methoxy group in Cephamycin C is introduced in two steps, i.e. via the action of a 7-hydroxylase enzyme on O-carbamoyldesacetylcephalosporin C to give the 7α-hydroxy derivative, followed by subsequent methylation.

As is now well Known, by means of recombinant DNA techniques, it is possible to insert into a host cell DNA carried on a vector with the result that the transformed host may become endowed with the capacity to synthesise whatever protein(s) or enzyme(s) the gene(s) carried on the insert DNA may encode. (For a full discussion of recombinant DNA methodology, and a glossary of the terms used therein, see 'Principles of Gene Manipulation' by R. W. Old and S. B. Primrose, 3rd Edition, Blackwell Scientific Publications, 1985).

The isolation and expression in *E. coli* of the isopenicillin N synthetase (cyclase) gene from *C. acremonium* has recently been reported by S. M. Samson et al (*Nature*, 1985, 318, 191–194).

In order to clearly define the invention reference is made to the accompanying drawings in which:

FIG. 1(*a*) is an endonuclease restriction map of *S. clavuligerus* ATCC 27064 chromosomal DNA (I) coding for genes involved in penicillin and cephalosporin biosynthesis;

FIG. 1(*b*) is an endonuclease restriction map of the portion of the DNA (I) contained in a plasmid designated pBROC 138;

FIG. 1(*c*) is an endonuclease restriction map of the portion of the DNA (I) contained in a plasmid designated pBROC 137;

FIG. 1(*d*) is an endonuclease restriction map of a portion of the DNA (I) contained in a plasmid designated pBROC 303;

Figures 1A, 1B, 1C, 1D:
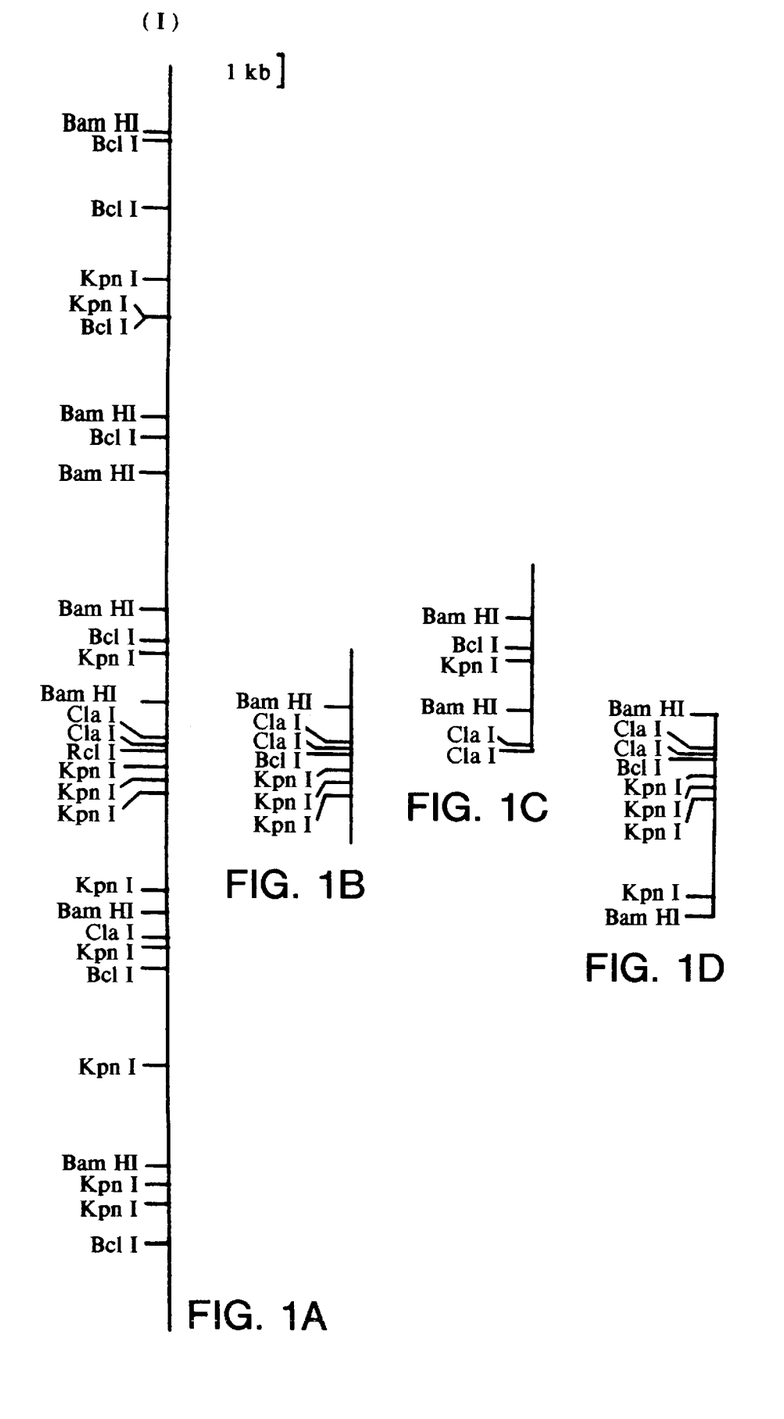

Accordingly, the present invention provides DNA (I) or a restriction fragment derived therefrom containing one or more genes coding for one or more enzymes involved in the biosynthesis of penicillin and cephalosporin β-lactams, the said DNA having the configuration of restriction sites hereinunder shown in FIG. 1(*a*).

The present invention further provides a recombinant vector capable of transforming a host cell, which vector contains insert DNA or a restriction fragment derived therefrom containing one or more genes coding for one or more enzymes involved in the biosynthesis of penicillin and cephalosporin β-lactams, the said DNA having the configuration of restriction sites hereinunder shown in FIG. 1(*a*).

Accordingly, in another aspect of the invention there is provided a host cell transformed with the recombinant vector of the invention. Suitably such host cells are micro-organisms, preferably *E. coli* or Streptomycetes, for example *S. lividans* 66 (DSM 1567).

As will be readily appreciated by those skilled in the art, it may not be convenient, or desired, to utilize the whole DNA segment (I) shown in FIG. 1(*a*) in the recombinant vector of the invention. Accordingly, suitable restriction fragments derived from the full length DNA (I) shown in FIG. 1(*a*) may be used as the insert DNA provided said suitable fragments contain one or more intact genes involved in the biosynthesis of penicillins and cephalosporins.

The restriction fragments according to the invention may be derived from the DNA segment (I) by cleavage with appropriate restriction enzymes by known methods.

Particularly preferred DNA fragments include those having the configuration of restriction sites shown in FIG. 1(*b*), FIG. 1(*c*) or FIG. 1(*d*) hereinbelow.

Figure 2:
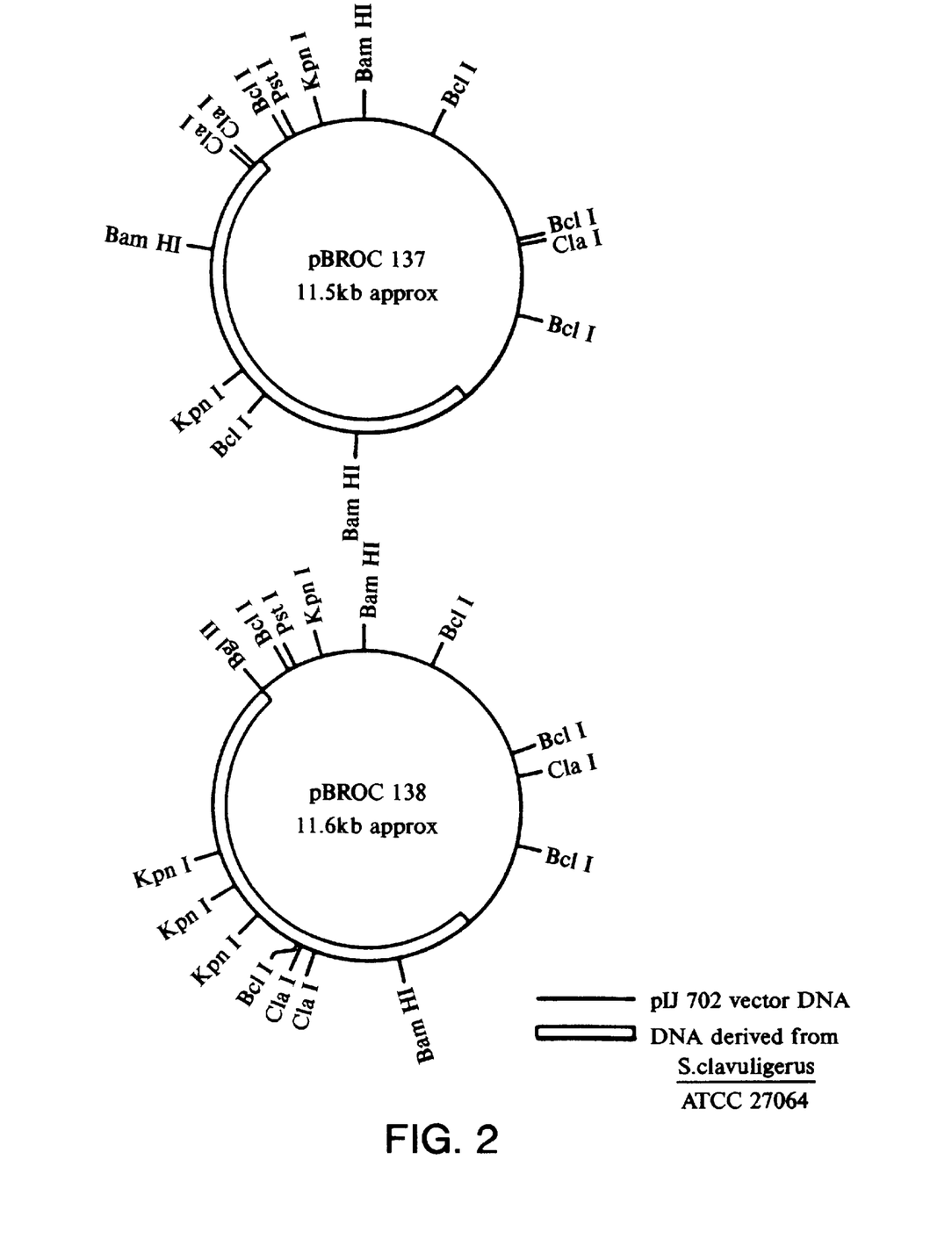
FIG. 2 is an endonuclease restriction map of plasmids pBROC 137 and pBROC 138.
Figure 3:
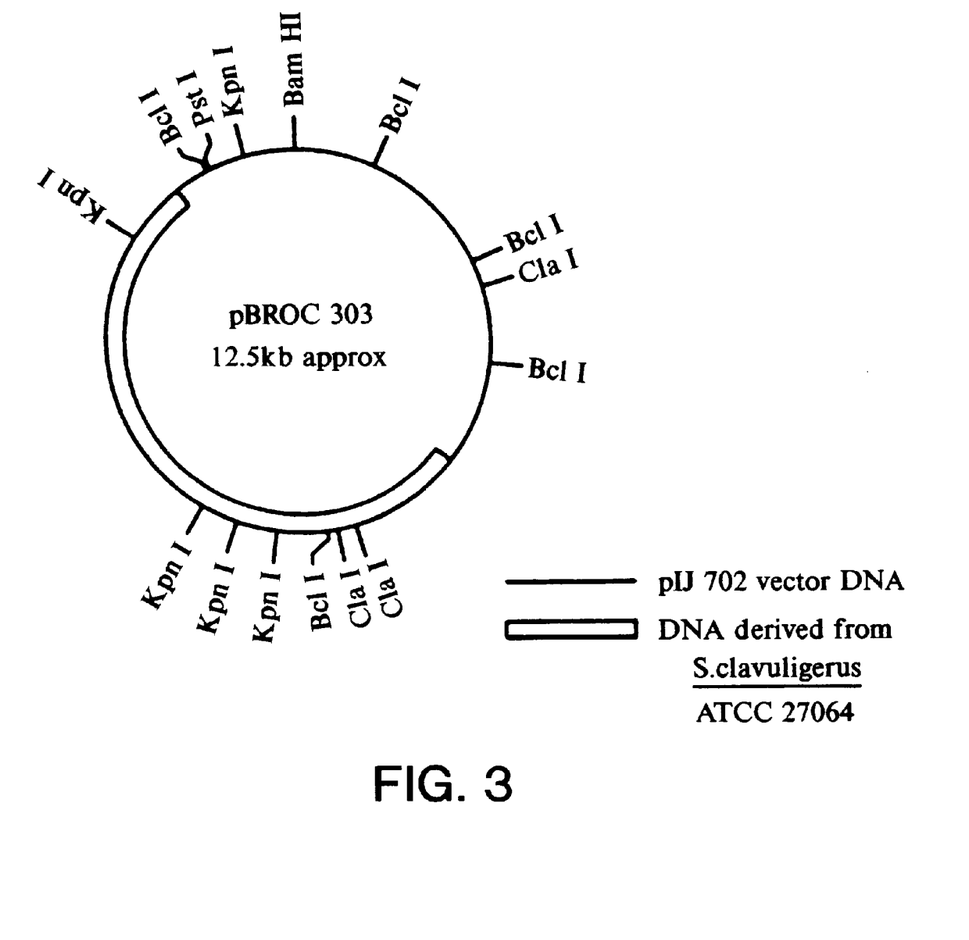
FIG. 3 is an endonuclease restriction map of plasmid pBROC 303.

In FIGS. 1 to 3 the abbreviations cla I, Bcl I etc. are conventional abbreviations for restriction endonucleases (see Old and Primrose, loc. cit.), and the approximate length in kilobases (Kb) of the DNA, as determined by sizing experiments carried out by agarose gel electrophoresis, is indicated. It should be understood that FIGS. 1 to 3 indicate the approximate positions of the restriction enzyme cleavage sites, as determined by such sizing experiments, and are not necessarily intended to show all the possible restriction sites present on the DNA illustrated.

The DNA characterized in FIG. 1(*a*), or a suitable restriction fragment derived therefrom such as the fragments illustrated in FIGS. 1(*b*), 1(*c*) and 1(*d*) may be ligated to any vector capable ot transforming any host cell in which the gene(s) coding for enzyme(s) involved in the biosynthesis of penicillins or cephalosporins may be expressed.

It will be understood that for the DNA of the invention to be expressed in such a host cell, the said DNA may either carry its own native promoter sequence which is recognised by an RNA polymerase of the host cell, or may be ligated to another suitable promoter sequence in a suitable fashion, or may be cloned at an appropriate restriction site, and in the correct translational reading frame, into a vector incorporating a suitable promoter sequence.

Suitable host cells in which the DNA of the invention may be expressed include *E. coli*, Penicillium species, Cephalosporium species, or Streptomyces species such as *S. clavuligerus* and *S. lividans*.

Normally the vector into which the DNA of the invention may be cloned is a plasmid, for example a plasmid derived from a Streptomycete, or is a temperate or virulent phage.

An example of a suitable vector is pIJ 702(molecular weight 8.9 megadaltons), a high copy number plasmid described by Katz, E. et al in J. Gen. Microbiol., 1983, 129, 2703–2714, and available from the John Innes Institute, Norwich, England.

An example of a suitable temperate phage is that known as φC31, described by Lomovskaya, N. D., Chater, K. F., Mkrtumian, N. M., in Bacteriol. Rev., 1980, 44, 206–229.

The recombinant vectors of the invention may be prepared by ligating the insert DNA characterized in FIG. 1(*a*), or a restriction fragment derived therefrom, to the chosen (linearized) vector by any convenient method, for example by direct combination of cohesive ends, homopolymer tailing, or by means of a linker or adapter molecule.

It will be appreciated that recombinant vectors prepared according to the above methods may contain the insert DNA in one of two possible orientations. Recombinant vectors containing both orientations are included within the scope of the invention.

Suitable recombinant vectors are plasmids containing the DNA fragments characterized by the configuration of restriction sites shown in FIGS. 1(*b*), 1(*c*) and 1(*d*) hereinbelow. Preferred recombinant vectors are those in which:

i) the DNA fragment shown in FIG. 1(*b*) is inserted into the Bgl II site of pIJ 702 (the construct is referred to hereinbelow as pBROC 138); or ii) the DNA fragment shown in FIG. 1(*c*) is inserted into the Bgl II site of pIJ 702 (the construct is referred to hereinbelow as pBROC 137); or iii) the DNA fragment shown in FIG. 1(*d*) is inserted into the Bgl II site of pIJ 702 (the construct is referred to hereinbelow as pBROC 303 ).

To prepare the DNA of the invention, a random array of DNA fragments may be generated by partial digestion of *S. clavuligerus* ATCC 27064 total cellular DNA by any convenient restriction enzyme. The endonuclease Sau 3AI (abbreviated hereinbelow to Sau 3A) and its isoschizomers are particularly suitable for this purpose.

The DNA fragments may then be size-fractionated on a sucrose gradient and fragments of length >3 Kb, preferably <15 Kb, may be isolated. Preferred fragments are of 4–14 Kb in size. The DNA fragments may then be ligated by conventional 'shot-gun' methods to a suitably cleaved vector, for example pIJ 702, and after recircularisation the recombinant vector may be transformed into a strain of *S. clavuligerus* which lacks the capability to produce Cephamycin C.

A suitable strain of *S. clavuligerus* for this purpose is *S. clavuligerus* NCP-5 which was deposited in the Beecham Culture Collection under the accession number BCC1 on Jan. 29, 1986 and later transferred to the National Collection of Industrial and Marine Bacteria, Aberdeen, Scotland, the deposit (NCIB 12208; filing date Feb. 19, 1986) being made under the terms of the Budapest Treaty on the International Recognition of the Deposit of Micro-organisms for the Purposes of Patent Procedure.

Accordingly, *S. clavuligerus* NCIB 12208 forms another aspect of the present invention.

The derivation and characteristics of *S. clavuligerus* NCP-5 (*S. clavuligerus* NCIB 12208) are as follows.

Derivation of *S. clavuligerus* NCP-5

Breaking out a sample of *S. clavuligerus* ATCC 27064 showed a variety of morphologies. Fourteen different types were recognised. One of these was isolated as *S. clavuligerus* SC-2. When cultured, *S. clavuligerus* SC-2 itself shows a variety of morphologies. From an example of the 'small' variety a 'large' colony variant was spontaneously derived, and designated *S. clavuligerus* NCP-5.

Taxonomy of *S. clavuligerus*, NCP-5

The taxonomical and morphological properties of *S. clavuligerus* NCP-5 were round to be essentially similar to those of *S. clavuligerus* ATCC 27064, a description of which may be found in U.S. Pat. No. 3,862,008 and also in Higgens, C. E. and Kastner, R. E., Int. J. Systematic Bacteriol., 1971, 21, 326–331. The method of culturing *S. clavuligerus* NCP-5 is similar to that described for *S. clavuligerus* ATCC 27064 in British Patent Specification No. 1 508 977.

The transformants obtained by the 'shot gun' methods hereinbefore described may be screened for their ability to produce Cephamycin C by bringing them into contact with a micro-organism sensitive to that compound and examining the growth characteristics of the said micro-organism. A suitable micro-organism for this purpose is *A. faecalis* (deposited in the National Collection of Industrial and Marine Bacteria under the Accession Number NCIB 8156 and also available to the public from the Beecham Culture Collection (accession number BCC2) at any time on request). For the purposes of the screening procedure the *A. faecalis* may be conveniently grown on agar plates, and a complementation assay may be carried out by inserting plugs of the transformants into the plates by conventional methods known in the art.

Transformants identified as 'positive' by their ability to produce zones of growth inhibition on media freshly seeded with a Cephamycin-sensitive micro-organism such as *A. faecalis* may be isolated and the recombinant vectors contained therein may be isolated from each 'positive' colony by conventional methods. On digestion of the recombinant vectors with suitable restriction enzymes, the *S. clavuligerus* DNA inserted into each vector may be identified, sized, and 'mapped' by cleavage with a variety of restriction enzymes in the conventional manner in order to check that it contains the DNA of the invention.

Two or more 'overlapping' inserts so isolated (i.e. inserts having common DNA) which are wholly or partly embraced within the DNA of the invention but are too small to contain intact genes involved in the biosynthesis of penicillins and cephalosporins may often be fused together by cleavage at a common restriction site followed by ligation (e.g. with DNA ligase) in the conventional manner to give, for example, the insert DNA of pBROC 137 and pBROC 138 or a suitable restriction fragment derived therefrom as hereinbefore defined.

The DNA (I) illustrated in FIG. 1(*a*) may be isolated by using the *S. clavuligerus* DNA of pBROC 137 or pBROC 138 to identify, by colony hybridization, *E. coli* cells carrying cosmids made from *S. clavuligerus* ATCC 27064 total cellular DNA and pHC79 (Hohn, B and Collins, J. (1980), *Gene*, 11, 291). The plasmid pBROC 303 may then be constructed from pIJ 702 and the DNA fragment illustrated in FIG. 1(*d*) [obtained from DNA (I)] by a simple subcloning procedure.

The production of enzymes involved in the biosynthesis of penicillins and cephalosporins may be achieved by re-inserting the DNA of the invention into a suitable vector, for example pIJ 702, and transforming a suitable host micro-organism, for example *S. lividans* 66 (DSM 1567), with the thus formed recombinant vector.

Particularly valuable enzymes so produced include those known in the art (J. F. Martin and P. Liras, loc. cit.) as 'cyclase' or isopenicillin N synthetase (capable of converting ACV into isopenicillin N), 'expandase' or deacetoxycephalosporin C synthetase (capable of converting penicillin N into deacetoxycephalosporin C), 'epimerase' or penicillin N synthetase (capable of converting isopenicillin N into penicillin N), and O-carbamoyldesacetylcephalosporin C-7-hydroxylase (capable of converting both O-carbamoyldesacetylcephalosporin C and cephalosporin C into their respective 7-hydroxy derivatives). Such enzymes of *S. clavuligerus* ATCC 27064, or any other proteins with the capability to bring about the synthesis of penicillins and cephalosporins, form another aspect of the present invention when produced by the transformed hosts of the invention. Preferably the proteins or enzymes are obtained in highly purified form.

Such proteins or enzymes may be isolated and purified by conventional methods.

The DNA of the invention and vectors containing same may find use in many areas of industrial activity. That also applies to host micro-organisms transformed with said vectors and the enzymes they express. For example the DNA may be utilised as a hybridization probe to identify and isolate related or overlapping genes present on the total cellular DNA of *S. clavuligerus* ATCC 27064 and of other micro-organisms which produce enzymes of similar structure and specificity.

Accordingly, the invention also provides the use of DNA (I) or any fragment thereof capable of hybridising to the DNA of a β-lactam antibiotic producing micro-organism for the purpose of isolating genes involved in β-lactam antibiotic biosynthesis in that organism.

Recombinant vectors containing the DNA of the invention may be of value, when transformed into suitable hosts, in the production of genetically modified micro-organisms which synthesize increased amounts of valuable antibiotics such as Cephamycin C, or in the generation of novel or hybrid antibiotics via the process of gene transfer (see for example D. A. Hopwood et al., *Nature*, 1985, 314, 642–644). Enzymes encoded by the DNA of the invention may be used, for example, in cell-free systems especially when immobilised on suitable solid supports to prepare known β-lactam antibiotics from their natural precursors or novel β-lactams from 'unnatural' precursors obtained, for example, by chemical synthesis.

The DNA of the invention or a fragment thereof (not necessarily carrying an intact gene) may be combined, either by recombinant DNA techniques or by natural recombination processes, with a fragment of a gene involved in β-lactam biosynthesis to produce a hybrid gene capable of directing the synthesis of a hybrid enzyme. Such enzymes may be used in the production of novel antibiotics by processes analogous to those hereinbefore described.

The DNA of the invention may also be modified by the known techniques of site-directed mutagenesis (in a manner analogous to that described, for example, by G. Winter et al., *Nature*, 1982, 299, 756–758; or by Zoller and Smith, *Nucleic Acids Research*, 1982, 10, 6487–6500) to give DNA in which specific mutations and/or deletions have been effected. The mutated DNA may be used to obtain an increased yield (or titre) of known β-lactam antibiotics from a suitable host micro-organism that already produces such compounds. The mutated DNA may also be used to obtain novel or hybrid antibiotics by gene transfer, or used in the production of mutant enzymes (muteins) which may be used in the production of novel antibiotics by analogous processes to those hereinabove described.

It will be understood that such mutated DNA is contemplated within the scope of the present invention.

The invention will now be illustrated by the following Examples.

EXPERIMENTAL

Preparation 1. Isolation of 4–15 kb size pieces of Sau 3A digested *S. clavuligerus* 27064 DNA (a) Total cellular DNA was prepared from *S. clavuligerus* 27064 in the following manner:
  i) Spores of *S. clavuligerus* 27064 were inoculated into 2 shake flasks of tryptone Soya Broth Maltose growth medium (30 ml/250 ml spring shake Flask—Trytone Soya Broth 30 g/l., Maltose 10 g/l) and incubated for 48 hours at 26° C. (240 rpm).
  ii) The mycelium was harvested by centrifugation at 10,000 G.
  iii) The supernatant fraction was poured off and the pellets resuspended in 10 ml of lysing solution (50 mM Tris pH 8.5, 50 mM $Na_2$ EDTA, 15% sucrose, lysozyme 3 mg/ml) and incubated for 1 hour at 37° C.
  iv) 0.5 ml Sodium Lauryl Sulphate (10% solution) containing 2 mg Proteinase K (ex SIGMA chemicals) was added and incubation continued for 15 minutes whereupon more SLS/Prot K solution was added and incubation was continued for a further 15 minutes.
  v) The DNA was spooled out on a glass rod after the addition of Na Acetate (to 0.3 M) and ice cold Ethanol (2 vols). This was repeated several times to give a translucent viscous preparation of DNA.

(b) Partial Sau 3A digestion of chromosomal DNA from *S. clavuligerus* 27064.

180 μg of total cellular DNA was incubated with 12 units of Sau 3 A restriction enzyme (NEW ENGLAND BIOLABS SUPPLIED) in the recommended buffer for 30 minutes at 37° C. The reaction was stopped by denaturing the enzyme at 70° C. When the extent of DNA digestion was examined by agarose gel electrophoresis it was found that the fragments ranged in size from 15 kb to 0.16 kb.

(c) Fractionation of Sau 3A partially digested DNA on a sucrose gradient 40% to 10% w/v.

A sucrose gradient (40–10%) was prepared in a 13 ml centrifuge tube as described in 'Genetic Manipulation of Streptomyces—A Laboratory Manual—authors; D. A. Hopwood et. al., published by the John Innes Foundation 1985'.

The Sau 3A partial digest of *S. clavuligerus* 27064 DNA (100 μg in 0.5 ml) was carefully layered on top of the sucrose gradient and the system centrifuged for 30,000 rpm ($10^5$ gav) for 21 hours.

The tube was removed from the centrifuge and fractions (400 μl) were collected from a pierced hole in the bottom of the tube. 5 μl samples of these fractions were examined by gel electrophoresis and those fractions shown to contain DNA of 4–14 kb in size were collected together. In this way 12 μg of Sau 3A digested DNA of 4–14 kb in size was obtained.

Preparation 2. Preparation of pIJ 702 Vector DNA suitable for cloning Sau 3A fragments of *S. clavuligerus* 27064 DNA (a) Isolation of plasmid DNA.

Spores of *S. clavuligerus* 27064:pIJ 702 were inoculated into TSB/Maltose medium in shake flasks (see Preparation 1(a) for make up of medium). Thiostrepton was added to 2.5 μg/ml to maintain plasmid stability. The micro-organism was grown for 48 hours at 26° C. pIJ 702 (Ref: Katz, E., et. al. *J. Gen. Microbiol.* (1983) 129 2703–2714) plasmid was isolated from the mycelium by use of the Neutral Lysis Procedure (see Hopwood et. al. 1985 loc. cit.). In this way 50 μg of pIJ 702 DNA was isolated.

(b) Bgl II Digestion of pIJ 702 DNA from *S. clavuligerus* 27064.

30 μg of pIJ 702 DNA was digested with Bgl II restriction enzyme (100 units as supplied by Amersham International) in a total volume of 400 μl of recommended restriction buffer for 30 minutes at 37° C.

The reaction was stopped by incubation at 70° C. for 30 minutes.

Examination of a sample of the reaction mix on agarose gel electrophoresis (0.7% gel) showed that all of the closed covalent circular (CCC) plasmid initially present nad been converted to linear form.

(c) Calf intestinal alkaline phosphatase (CIAP) treatment of Bgl II digested pIJ 702 DNA.

This was carried out as described in 'Molecular Cloning—A Laboratory Manual, Maniatis, T. et. al. publisher by Cold Spring Harbour Laboratory (1982)'

Examination of the CIAP treated DNA in the presence of T4 DNA ligase showed that it would no longer self-ligate after the enzymatic dephosphorylation had been carried out.

Preparation 3. Ligation of Sau 3A digested total cellular DNA of *S. clavuligerus* 27064 with Bgl II digested, CIAP treated pIJ 702 DNA.

To each of 12 containers containing 1 μg of Sau 3A digested *S. clavuligerus* 27064 chromosomal DNA (4–14 kb) in 50 μl of water was added 100 μl of Bgl II digested, CIAP treated pIJ 702 (0.5 μg/pot) in buffer to give final concentrations of 1.5 μg DNA/150 μl, Tris. HCl pH 7.5 (66 mM), $MgCl_2$ (6.6 mM), Dithiothreitol (10 mM) and Adenosine Triphosphate (0.4 mM). T4 DNA LIGASE (0.1 unit—as supplied by Amersham International) was added to each pot and the systems incubated at 15° C. for 72 hours before transformation into the required recipients.

Preparation 4. Formation of a Library of *S. clavuligerus* NCP-5. pIJ 702/27064 clones (a) Testing the ligated DNA in *S. lividans* 66 for frequency of inserted DNA into pIJ 702 and size of DNA inserts.

1.5 μg of ligated DNA (4–14 kb Sau 3 A generated fragments of *S. clavuligerus* 27064 ligated with Bgl II digested, CIAP treated pIJ 702 prepared from *S. clavuligerus* 27064) was dissolved in 10 μl TE buffer (1 mM $Na_2$ EDTA, 10 mM Tris. HCl pH 8.2) and used as 2×5 μl aliquots in the transformation of 2×100 μl volumes of *S. lividans* 66 (DSM 1567) protoplasts ($10^{10}$ protoplasts/ml—prepared as described in 'Genetic Manipulation of Streptomyces—A Laboratory Manual'—in the presence of 25% polyethylene glycol (average molecular weight 1000).

After transformation the protoplasts were plated out at dilutions of up to $10^{-4}$ on R2YE agar (see Hopwood et. al., loc cit).

After incubation at 32° C. for 24 hours the plates were overpoured with soft nutrient broth (SNBA) agar (8 g Difco Nutrient Broth/l, 3 g agar/1 containing Thiostrepton antibiotic (500 μg/ml) to select for plasmid bearing colonies and also containing L-Tyrosine (1 g/1) to detect those colonies bearing plasmids with inserts in the mel gene of pIJ 702.

After several days of growth the frequency of black colonies (less than 2%) and the transformation efficiency of the ligated DNA (9.3×103 transformants/μg DNA) could be ascertained by counting.

Plasmids were prepared from 10 of the white *S. lividans* 66 colonies in the manner previously described (Preparation 2a). These plasmid preparations were digested with Bcl I restriction enzyme with subsequent agarose gel electrophoresis in order to determine the size of DNA inserts.

It was determined in this fashion that the average size of DNA cloned was 5 kb.

(b) Transformation of a Ligated DNA Sample into *S. clavuligerus* NCP-5 (*S. clavuligerus* NCIB 12208)

1.5 μg of ligated DNA was transformed in 2×5 μl of T.E. buffer into 2×100 μl of *S. clavuligerus* NCP-5 protoplasts ($10^{10}$ protoplasts/ml, prepared as in Hopwood et. al., (1985) loc. cit. The transformed protoplasts were regenerated at 26° C. on R5 agar (100 g sucrose/l, 10 g dextrin/l, 5.1 g $MgCl_2.6H_2O$/l, 1 g Casamino acids/l, 0.05 g $MgSO_4.7H_2O$/l, 2.5 g L-Arginine HCl/l, 1 ml trace elements/l, 20 g Oxoid Technical Agar no. 3/1, 0.05 g $KH_2PO_4$/l, 3.7 g $CaCl_2.2H_2O$/l, 5.7 g TES buffer pH 7.2/l. Trace elements solution consisted of $FeSO_4.7H_2O$ 1 g/l, $MnCl_2.4H_2O$ 1 g/l, $ZnSO_4.7H_2O$ 1 g/l). Thiostrepton resistant colonies were selected by overlaying with SNBA (as described in Preparation 4a) containing Thiostrepton (50 μg/ml) after 48 hours of regeneration. After a further 72 hours the transformed colonies were individually scraped, in arrays onto a nutrient agar suitable for antibiotic production (M5D$^+$ agar containing Dextrin 10 g/l, $K_2HPO_4$ 1 g/l, $MgSO_4.7H_2O$ 1 g/l, $(NH_4)_2SO_4$ 1 g/l, Industrial Chalk 4 g/l, Trace Element solution 1 ml/l, Agar 20 g/l, yeast extract 2 g/l and Bacteriological peptone 2.5 g/l. The trace element solution consists of $FeSO_4.7H_2O$ 0.1%, $MnCl_2.4H_2O$ 0.1% and $ZnSO_4.7H_2O$ 0.1%) and containing Thiostrepton (2.5 μg/ml).

4500 NCP-5 colonies which displayed Thiostrepton resistance conferred by pIJ 702: *S. clavuligerus* 27064 DNA plasmids were obtained in this manner.

Preparation 5. Screening the NCP-5: pIJ 702/*S. clavuligerus* 27064 Library for Production of Cephamycin C.

After 10 days of growth on M5D$^+$ agar at 26° C., 8 mm diameter agar plugs were cut from each of the mycelial patches and placed upon DST agar (40 g Oxoid DST agar/l water) which had been freshly seeded with *Alcaligenes faecalis* ATCC 8750/NCIB 8156. (See Claridge, C. A. and Johnson, D. L. (1962) *Antimicrob. Ag. Chemother.* 682–686)). This organism is sensitive to certain cephalosporins such as cephalosporin C and cephamycin C but not penicillin N even in the presence of the low levels of clavulanic acid produced by NCP-5 under the growth conditions used, consequently NCP-5 which produced penicillin N and clavulanic acid only normally gives no zone of inhibition of growth on *A. faecalis* NCIB 8156 whereas its parent *S. clavuligerus* strain does (as it produces penicillin N, clavulanic acid and Cephamycin C). The antibiotic from the plugs was allowed to diffuse into the DST/*A. faecalis* agar and after overnight incubation at 37° C. the *A. faecalis* growth examined for zones of antibiosis.

In this way, possible production of Cephalosporin antibiotics by any of the members of the library of clones was searched for. Two of the clones labelled NCP-5/36/5 and NCP-5/10/7 were found to give zones of antibiosis against *A. faecalis*.

Preparation 6. Examination of the Plasmid Content of NCP-5/36/5 and NCP-5/10/7.

(a) Physical Examination of the Plasmids

Plasmid preparations were made from NCP-5/36/5 and NCP-5/10/7 as described in Preparation 2a. It was possible to isolate several micrograms of plasmid material from 30 ml cultures of each of the two positives. Restriction enzyme site mapping showed clearly that only a single species of plasmid was present in NCP-5/36/5 and also only a different single species in NCP-5/10/7. Restriction Mapping (see FIG. 1) suggested that the plasmids pBROC 137 and pBROC 138 isolated from NCP-5/36/5 and NCP-5/10/7 respectively contained approximately 5.7 kb and approximately 5.8 kb DNA inserts in pIJ 702. The two DNA inserts appeared to contain a common fragment of approximately 2.7 kb as suggested by mapped restriction enzyme sites and this was subsequently proved by showing extensive hybridization of the respective $^{32}$P labelled fragment of pBROC 138 to the predicted portion of pBROC 137 DNA using Southern analysis.

(b) Reintroduction of the plasmids pBROC 137 and pBROC 138 into NCP-5.

100 nanogram amounts of pBROC 137 and pBROC 138 DNA were used to retransform S. clavuligerus NCP-5. The transformed colonies were isolated and subsequently tested upon A. faecalis bioassay plates as described in Preparation 5.

It was apparent that at least 90% of all of the NCP-5 colonies retransformed with pBROC 137 or pBROC 138 were now able to give zones of antibiosis on A. faecalis. This confirmed that the DNA present in pBROC 137 and pBROC 136 contained genetic information able to repair the mutation incurred with NCP-5.

Preparation 7. The Assay of Novel Enzymatic Activities Conferred upon *Streptomyces Lividans* 66 by pBROC 137, pBROC 138, and pBROC 303

100 nanogram quantities of PBROC 137 DNA, pBROC 138 DNA and pBROC 303 DNA transformed into S. *lividans* 66 (as in Preparation 4a).

Cultures of S. *lividans* 66: pBROC 137, S. *lividans* 66 pBROC 138, and S. *lividans* 66: pBROC 303 were grown in shake flasks of YEME (30 ml glucose 10 g/l, Sucrose 340 g/l, malt extract 3 g/l, Bacteriological Peptone 5 g/l, yeast extract (Oxoid) 3 g/l, containing Thiostrepton antibiotic at 50 μg/ml. The cultures were grown for 48 hours at 32° C. at 240 rpm. Mycelium was harvested by centrifugation at 10,000 g and washed with Tris. HCl buffer pH 7.0 (0.05 M). The mycelium was recentrifuged and the pellet resuspended in 2.5 ml Tris. buffer. Cell disruption was carried out by use of a French Pressure Cell at 1000 psi and the broken cell preparations centrifuged at $10^5$ g for 60 minutes to furnish a cell free, particulate free soluble enzyme preparation.

(a) Demonstration of Expandase Enzymic Activity

Enzyme preparations from S. *lividans* 66:pIJ 702, S. *lividans* 66: pBROC 137 and S. *lividans* 66: pBROC 138 were used in ring expansion assay systems (as described in Jensen, S. E., Westlake, D. W. S. and Wolfe, S., (1983) *Antimicrob. Ag. Chemother.* 24(3) 307–312) to determine the presence of deacetoxycephalosporin C synthetase.

Utilizing the E. coli ESS/Penicillinase (DIFCO Penicillinase Concentrate $10^4$ u/ml) bioassay system described by these authors it could be shown that the S. *lividans* 66: pIJ 702 extracts were unable to transform Penicillin N to penicillinase resistant antibiotics whereas the extracts from S. *lividans* 66 pROC 137 and S. *lividans* 66: pBROC 138 were able to carry out that transformation. S. *lividans* 66: pBROC 137 enzyme extracts were able to carry out a substantial transformation of the penicillin N in the assay system to penicillinase resistant antibiotic whereas the enzyme extract from S. *lividans* 66: pBROC 138 exhibited much lower activity in this respect. Subsequently the ring expansion assays were chromatographed on cellulose t.l.c. plates (Butanol/Acetic Acid/Water, 3/1/1) together with authentic samples of penicillin N, deacetoxy cephalosporin C and deacetyl cephalopsorin C. Bioassay of the chromatograms on E. coli ESS/Difco Penicillinase containing agar showed, after overnight incubation at 37° C., that S. *lividans* 66: pBROC 137 enzyme extracts had transformed penicillin N into deacetoxy Cephalosporin C whereas extracts of enzyme from S. *lividans* 66: pIJ 702 did not. No deacetyl cephalosporin C was identified as being synthesized from penicillin N by any of the cell extracts. (Rf of deacetoxy cephalosporin C=0.55; Rf of deacetyl Cephalosporin C=0.39.). (Penicillin N is not detected due to presence of penicillinase).

(b) The Conversion of iso-Penicillin N to a chemical form more active against E. coli ESS.

Using the iso-Penicillin N epimerase assay developed by Jensen, S. E. et. al. (*Can. J. Microbiol.* (1983) 29(11) 1526–1531) it was possible to demonstrate that a cell free, particulate free enzyme extract (as in Preparation 7a) from S. *lividans* 66: pBROC 137 was able to convert iso-Penicillin N to a chemical form at least ten times more active against E. coli ESS than iso-Penicillin N itself. A similar extract from S. *lividans* 66: pIJ 702 was unable to do this.

(c) The conversion of O-Carbamoyl Desacetyl Cephalosporin C and Cephalosporin C to their 7-Hydroxy derivatives by cell free preparations of S. *lividans* 66: pBROC 303.

Cell free preparations of S. *lividans* 66: pBROC 303 (0.9 ml) were incubated at 22° C. with Sodium Ascorbate (2.8 mM), Ferrous Sulphate (0.045 mM), α-ketoglutarate (1 mM), Potassium Chloride (7.5 mM), Magnesium Sulphate (7.5 mM), Tris-hydrochloride pH 7.0 (0.05 M), and either O-Carbamoyl Desacetyl Cephalosporin C (0.5 mM) or Cephalosporin C (0.5 mM) in a final volume of 1.2 ml.

After 2 hours of incubation, 25 μl of Glacial Acetic Acid was added with shaking and a de-proteinated supernatant was obtained by centrifugation (10,000 G for 5 minutes). This liquid was absorbed onto a QAE-Sephadex column (1 ml volume). The resin was washed with 250 μl of water and 200 μl of 0.2 M NaCl.

The cephalosporins were eluted from the resin with a further 250 μl of 0.2 M NaCl.

20 μl samples of these concentrated reaction products were analysed by High Performance Liquid Chromatography using $C_{18}$ reverse-phase Microbondapak columns. The mobile phase for the separation of O-Carbamoyl Desacetyl Cephalosporin C from 7-Hydroxy O-Carbamoyl Desacetyl Cephalosporin C was 0.1 M $NaH_2PO_4$, pH 3.2. To separate Cephalosporin C from 7-Hydroxy Cephalosporin C the pH of the mobile phase was increased to 4.2 Elution was carried out at 2 ml/minute with U.V. detection at 260 n.m.

In this manner it was possible to demonstrate approximately 50% conversion of O-Carbamoyl Desacetyl Cephalosporin C (retention time 5.7 minutes) to its 7-Hydroxy derivative (retention time 3.0 minutes) and approximately 35% conversion of Cephalosporin C (retention time 18.2 mins) to 7-Hydroxy Cephalosporin C (retention time 6.6 minutes). Extracts of S. *lividans* 66: pIJ 702 were unable to carry out these transformations.

Preparation 8. Sodium Lauryl Sulphate/Polyacrylamide Gel Electrophoresis of Proteins produced by S. *lividans* 66: pBROC 137 and S. *lividans* 66 pBROC 138.

Volumes (5 μl, 10 μl) of cell free, particulate free extracts of S. *lividans* 66: pBROC 137, S. *lividans* 66 pBROC 138 and S. *lividans* 66: pIJ 702 (as in Preparation 7a) were treated with sodium lauryl sulphate (SLS) to denature the proteins in solution and chromatographed by SLS/12% Polyacrylamide Gel Electrophoresis using the method of Laemmli, U.K. (*Nature* (1970) 227 680). Staining with Coomassie Brillant Blue revealed that as could be judged from proteins of known molecular weight co-chromatographed, the extracts from S. lividans 66: pBROC 137 and S. lividans 66: pBROC 138 displayed a protein of approximately 29,500 Daltons which was either not present or very much fainter in the extract from S. lividans 66: pIJ 702. The extract from S. lividans 66: pBROC 137 also displayed a prominently staining protein band at approximately 60,000 Daltons in size.

Preparation 9. The Isolation, Characterization and Subcloning of DNA from the S. clavuligerus chromosome contiguous with that DNA contained in pBROC 137 and pBROC 138 a) Construction of a library of S. clavuligerus ATCC 27064 DNA in pHC 79.

10 μg of pHC 79 DNA (Holm, B. and Collins, J (1980) Gene 11, 291–298) was digested to completion with restriction enzymes Sal I and Bam HI. A further 10 μg of pHC 79 DNA was digested to completion with Eco RI and Bam HI. To isolate the required 'cosmid arms' both digests were fractionated on a sucrose gradient (10–40%). The yield of each cosmid arm was >5 μg.

100 μg of S. clavuligerus ATCC 27064 chromosomal DNA was partially digested with Sau 3A I and fractionated on a sucrose gradient (10–40%). Fractions containing restriction fragments >30 Kb and <50 Kb were pooled thus providing approximately 10 μg of Sau 3A I fragments in this size range. These fragments were ligated to the cosmid arms at a molar ratio of 1:1:1 (DNA concentration 200 μg ml$^{-1}$). After 24 hours the ligation mix was packaged in vitro into lambda phage. (Phage lambda packaging extracts and protocol supplied by Amersham International PLC). Transfection of E. coli DHI (Low, B. (1968) PNAS 60, 161–167) yielded 5×10$^7$ transfectants/μg packaged DNA.

b) Isolation of DNA segment (I) from the S. clavuligerus ATCC 27064 DNA library and subcloning this DNA into pIJ 702.

5000 E. coli DHI colonies containing pHC 79 with S. clavuligerus ATCC 27064 DNA inserts were immobilized and lysed on nitrocellulose filters. The 1.2 Kb Bcl I—Kpn I ended fragment from pBROC 137 was isolated and nick translated. This fragment was used to probe the filters by standard colony hybridization techniques. Seven hybridizing colonies were obtained, one of which contained DNA segment (I) illustrated in FIG. 1(a).

Subcloning fragments of DNA segment (I) was effected by first digesting 10 μg of this cloned DNA with Bam HI. 5 μg of the vector, pIJ 702, was digested with Bgl II and treated with CIAP to prevent recircularization. The Bam HI generated fragments were ligated to the Bgl II digested, CIAP treated pIJ 702 at a molar ratio of 2:1 respectively and a DNA concentration of 50 μg ml$^{-1}$. After incubation at 15° C. for 24 hours 0.5 μg of ligation mix was transformed into S. lividans 66 and 2×10$^5$ transformants/μg obtained. Screening the transformants permitted the isolation of pBROC 303 together with the other Bam HI fragment clones.

We claim:

1. An isolated DNA (I) segment having a nucleotide sequence endogenous to Streptomyces clavuligerus ATCC 27064 or a restriction fragment derived therefrom, comprising one or more genes coding for one or more enzymes directly involved in the biosynthesis of penicillin and cephalosporin β-lactams, said enzyme selected from the group consisting of penicillin N synthetase, deacetoxy cephalosporin C synthetase, and O-carbamoyldesacetylcephalosporin C-7-hydroxylase, said DNA (I) having the configuration of restriction sites shown in FIG. 1(a).

2. DNA according to claim 1 having the configuration of restriction sites shown in FIG. 1(b), FIG. 1(c) or FIG. 1(d).

3. A recombinant vector comprising a DNA sequence according to claim 1.

4. A recombinant vector comprising a DNA sequence as claimed in claim 1 cloned into a plasmid derived from a Streptomycete or a temperate phage.

5. A recombinant vector according to claim 4 in which the plasmid is pIJ 702.

6. A recombinant vector comprising an isolated DNA segment or restriction fragment according to claim 2.

7. A recombinant vector according to claim 6 selected from the group consisting of pBROC 137, pBROC 138 and pBROC 303.

8. A host cell transformed with at least one recombinant vector as claimed in claim 3.

9. A host according to claim 8 in which the host is a Streptomycete.

10. A host according to claim 8 in which the host is S. lividans 66 (DSM 1567).

11. A host cell transformed with at least one recombinant vector as claimed in claim 6.

12. A host cell according to claim 11 in which the host is a Streptomycete.

13. A host cell according to claim 11 in which the host is S. lividans 66 (DSM 1567).

14. A method for expressing, in a recombinant host cell, an enzyme selected from the group consisting of penicillin N synthetase, deacetoxy cephalosporin C synthetase, and O-carbamoyldesacetylcephalosporin C-7-hydroxylase, said method comprising:

A. transforming said host cell with a recombinant DNA expression vector comprising the DNA (I) segment having a nucleotide sequence endogenous to Streptomyces clavuligerus ATCC 27064, or restriction fragment thereof, said DNA (I) having the configuration of restriction sites shown in FIG. 1(a); and B. culturing the transformed host cell of step A. under conditions suitable for expression of said enzyme.

15. The method of claim 14, wherein said DNA segment, or restriction fragment thereof, has a configuration of restriction sites shown in any of FIG. 1(b), FIG. 1(c), or FIG. 1(d).

16. The method of claim 14, wherein said vector comprises DNA coding for deacetoxycephalosporin C synthetase.

17. The method of claim 14, wherein said vector comprises DNA coding for penicillin N synthetase.

18. The method of claim 14, wherein said vector comprises DNA coding for O-carbamoyldesacetylcephalosporin C-7-hydroxylase.

19. The method of claim 14, wherein said host cell is selected from the group consisting of E. coli, Cephalosporium, Streptomyces, and Penicillium.

20. The method of claim 14, wherein said host cell is E. coli.

21. The method of claim 14, wherein said host cell is Cephalosporium.

22. The method of claim 14, wherein said host cell is Streptomyces.

23. The method of claim 22, wherein said host cell is Streptomyces clavuligerus.

24. The method of claim 22, wherein said host cell is Streptomyces lividans.

25. The method of claim 14, wherein said host cell is Penicillium.

26. In a process for the isolation or purification of genes from a micro-organism, said genes involved in β-lactam antibiotic biosyntheses, the improvement which comprises the use of DNA (I) endogenous to *Streptomyces clavuligerus* or any fragment thereof capable of hybridizing to the DNA of said β-lactam antibiotic producing micro-organism to identify said genes for isolation or purification.

27. An isolated enzyme capable of converting isopenicillin N into penicillin N and said enzyme having been produced by a transformed host as claimed in claim 8.

28. An isolated enzyme capable of converting O-carbamoyldesacetylcephalosporin C into O-carbamoyldesacetyl- 7-hydroxycephalosporin C and said enzyme having been produced by a transformed host as claimed in claim 8.

29. *S. clavuligerus* NCIB 12208.

* * * * *